United States Patent [19]

Okada et al.

[11] Patent Number: 6,113,943

[45] Date of Patent: Sep. 5, 2000

[54] SUSTAINED-RELEASE PREPARATION CAPABLE OF RELEASING A PHYSIOLOGICALLY ACTIVE SUBSTANCE

[75] Inventors: Hiroaki Okada; Yayoi Douken, both of Osaka, Japan

[73] Assignee: Takeda Chemical Industries, Ltd., Osaka, Japan

[21] Appl. No.: 08/962,347

[22] Filed: Oct. 31, 1997

[30] Foreign Application Priority Data

Oct. 31, 1996 [JP] Japan .................................... 8-290441

[51] Int. Cl.[7] .............................. A61K 9/50; A61K 9/52; A61K 9/14

[52] U.S. Cl. ......................... 424/457; 424/451; 424/452; 424/423; 424/425; 424/486; 424/489; 514/963; 514/965

[58] Field of Search ..................................... 424/426, 451, 424/455, 457, 450, 486, 489, 423, 425; 428/402.21, 402.24; 514/963, 965

[56] References Cited

U.S. PATENT DOCUMENTS

| | | | |
|---|---|---|---|
| 3,773,919 | 11/1973 | Boswell et al. | 424/19 |
| 5,476,663 | 12/1995 | Okada et al. | 424/423 |
| 5,631,020 | 5/1997 | Okada et al. | 424/451 |
| 5,631,021 | 5/1997 | Okada et al. | 424/451 |

FOREIGN PATENT DOCUMENTS

| | | |
|---|---|---|
| 0 052 510 | 5/1982 | European Pat. Off. |
| 0 058 481 | 8/1982 | European Pat. Off. |
| 0 145 240 | 6/1985 | European Pat. Off. |
| 0 190 833 | 8/1986 | European Pat. Off. |
| 0 244 114 | 11/1987 | European Pat. Off. |
| 0 251 476 A1 | 1/1988 | European Pat. Off. |
| 0 330 180 | 8/1989 | European Pat. Off. |
| 0 442 671 | 8/1991 | European Pat. Off. |
| 0 442 671 A2 | 8/1991 | European Pat. Off. |
| 0 442 671 B1 | 8/1991 | European Pat. Off. |
| 0 474 098 A1 | 3/1992 | European Pat. Off. |
| 0 586 238 | 3/1994 | European Pat. Off. |
| 0 586 238 A2 | 3/1994 | European Pat. Off. |
| 0 601 799 A1 | 6/1994 | European Pat. Off. |
| 0 669 128 A1 | 8/1995 | European Pat. Off. |
| 96/10397 | 4/1996 | WIPO. |

OTHER PUBLICATIONS

Y. Aso et al., "Effect of Temperature on Mechanisms of Drug Release and Matrix Degradation of Poly(D,L–lactide) Microspheres", Journal of Controlled Release, vol. 31, pp. 33–39, 1994.

Y. Tabata et al., "A Formulation Method Using D,L–lactic Acid Oligomer for Protein Release with Reduced Initial Burst", Journal of Controlled Release, vol. 23, pp. 55–64, 1993.

*Primary Examiner*—Thurman K. Page
*Assistant Examiner*—Brian K. Seidleck
*Attorney, Agent, or Firm*—Wenderoth, Lind & Ponack, L.L.P.

[57] ABSTRACT

Disclosed is a sustained-release preparation comprising 1) a polymer of lactic acid having a weight-average molecular weight of about 25,000 to about 60,000 and 2) a physiologically active substance, and which releases the physiologically active substance over a period of at least about 5 months; the sustained-release preparation shows an almost continuous zero order release of the physiologically active substance over a period of as long as about 5 months.

18 Claims, No Drawings

SUSTAINED-RELEASE PREPARATION CAPABLE OF RELEASING A PHYSIOLOGICALLY ACTIVE SUBSTANCE

BACKGROUND OF THE INVENTION

1. Field of the Invention

The present invention relates to a sustained-release preparation which releases a physiologically active substance over a period of at least about 5 months.

2. Description of Related Art

A microsphere-type sustained-release preparation of drugs containing a biodegradable polymer is described in JP-A 118512/1982 (EP-A 52510), 150609/1982 (EP-A 58481), 100516/1985 (EP-A 145240), 201816/1987 (EP-A 190833), 321622/1992 (EP-A 442671) and 97334/1995 (EP-A 601799), for instance. Especially in JP-A 100516/1985 (EP-A 145240) and 201816/1987 (EP-A 190833), production of sustained-release microcapsules of a water-soluble drug with good dispersibility and high entrapment ratio by an in-water drying method is described. In JP-A 321622/1992 (EP-A 442671), long-term sustained-release microcapsules designed for zero order release of a polypeptide over a period of at least 2 months and containing a copolymer or homopolymer having a lactic acid/glycolic acid ratio of 80/20 to 100/0 and having a weight-average molecular weight of 7,000 to 30,000 are described.

SUMMARY OF THE INVENTION

The present invention relates to (1) sustained-release preparation comprising 1) a polymer of lactic acid having a weight-average molecular weight of about 25,000 to about 60,000 and 2) a physiologically active substance, and which releases the physiologically active substance over a period of at least about 5 months;

(2) the preparation according to the above (1), wherein the polymer of lactic acid is obtained by hydrolyzing a polylactic acid produced by ring-opening polymerization;

(3) the preparation according to the above (1), wherein the polymer of lactic acid is substantially free from a catalyst;

(4) the preparation according to the above (1), wherein the polymer of lactic acid has a weight-average molecular weight of about 30,000 to about 50,000;

(5) the preparation according to the above (1), wherein the polymer of lactic acid has a dispersity of about 1.2 to about 4.0;

(6) the preparation according to the above (1), which is for injection;

(7) the preparation according to the above (1), which further comprises an excipient;

(8) the preparation according to the above (7), wherein the excipient is sugar;

(9) the preparation according to the above (1), wherein the physiologically active substance is a physiologically active peptide;

(10) the preparation according to the above (9), wherein the physiologically active peptide is a LHRH agonist or a LHRH antagonist;

(11) the preparation according to the above (10), wherein the LHRH agonist is a peptide represented by the formula:

$$(Pyr)Glu-R_1-Trp-Ser-R2-R3-R4-Arg-Pro-R5 \quad (I)$$

wherein $R_1$ represents His, Tyr, Trp or p-NH$_2$-Phe; $R_2$ represents Tyr or Phe; $R_3$ represents Gly or an optionally substituted D-type amino acid residue; $R_4$ represents Leu, Ile or Nle; $R_5$ represents Gly-NH-$R_6$ wherein $R_6$ is hydrogen or an alkyl group with or without hydroxy group or NH-$R_7$ wherein $R_7$ is hydrogen, an alkyl group with or without amino or hydroxy group, or ureido, or a salt thereof;

(12) the preparation according to the above (11), wherein the peptide represented by the formula (I) or a salt thereof is leuprorelin or leuprorelin acetate;

(13) the preparation according to the above (1), wherein the physiologically active substance is contained in an amount of about 0.01 to about 50% (w/w);

(14) the preparation according to the above (1), wherein the ratio of the physiologically active substance relative to the polymer of lactic acid is about 0.01 to about 50% (w/w);

(15) the preparation according to the above (1), wherein the physiologically active substance is leuprorelin acetate, the polymer of lactic acid has a weight-average molecular weight of about 28,400 to about 47,800, and the preparation releases leuprorelin acetate over a period of at least about 6 months; and

(16) method of producing a sustained-release preparation releasing a physiologically active substance over a period of at least about 5 months, which comprises subjecting to microencapsulation a w/o emulsion with a solution containing a physiologically active substance as an internal aqueous phase and with a solution containing a polymer of lactic acid having a weight-average molecular weight of about 25,000 to about 60,000 as an oil phase.

DETAILED DESCRIPTION OF THE INVENTION

In the present specification, regarding references to "weight-average molecular weight" and "dispersity", the present inventors intend that the former be measured in terms of polystyrene as determined by gel permeation chromatography (GPC) using 9 polystyrenes as reference substances with weight-average molecular weights of 120,000, 52,000, 22,000, 9,200, 5,050, 2,950, 1,050, 580 and 162, respectively, and that the latter be calculated therefrom. The above determination was carried out using a GPC column KF804L (produced by Showa Denko, Japan)×2 and an RI monitor L-3300 (produced by Hitachi, Ltd., Japan), with chloroform as a mobile phase.

Regarding abbreviations for amino acids, protecting groups and others, abbreviations used in the present specification are based on abbreviations specified by the IUPAC-IUB Commission on Biochemical Nomenclature or abbreviations in common use in relevant fields. When an optical isomer may be present in amino acid, it is of the L-configuration, unless otherwise stated.

Abbreviations used in the present specification are defined as follows:

NAcD2Nal: N-acetyl-D-3-(2-naphthyl)alanyl
D4ClPhe: D-3-(4-chlorophenyl)alanyl
D3Pal: D-3-(3-pyridyl)alanyl
NMeTyr: N-methyltyrosyl
DLys(Nic): D-(epsilon-N-nicotinoyl)lysyl Lys(Nisp): (Epsilon-N-isopropyl)lysyl DhArg(Et$_2$): D-(N,N'-diethyl)homoarginyl The polymer of lactic acid used in the present invention is a biodegradable polymer which decomposes in a living body over a period of at least about 5 months and has a free terminal carboxyl group. The present polymer is a homopolymer of lactic acid.

The weight-average molecular weight of the present polymer of lactic acid is about 25,000 to about 60,000, preferably about 27,000 to about 55,000, more preferably about 28,000 to about 50,000. Employment of these ranges of the weight-average molecular weight enables production of a sustained-release preparation showing a small initial burst of drugs and a continuous zero order release of drugs.

The dispersity (weight-average molecular weight/number-average molecular weight) of the polymer of lactic acid used in the present invention is preferably about 1.2 to about 4.0, more preferably about 1.5 to about 3.5.

The present polymer of lactic acid may be of the L-, D- or DL-configuration, with preference given to the DL-configuration. Regarding the DL-configuration, the ratio of the D-configuration/L-configuration (mol %) is preferably about 75/25 to about 20/80, more preferably about 60/40 to about 25/75, still more preferably about 55/45 to about 25/75.

The polymer of lactic acid used in the present invention is preferably produced by hydrolyzing a starting polylactic acid produced by ring-opening reaction of a cyclic dimer of lactic acid and polymerization.

The starting polylactic acid produced by the ring-opening reaction and polymerization is a polymer of a high molecular weight region, which is not obtained by a dehydration condensation of lactic acid wherein heating is conducted under reduced pressure after addition of a catalyst (JP-A 45920/1981, EP-A 26599), or a method for producing a polymer which is obtained by polymerization of lactic acid without using a catalyst and is substantially free from a catalyst (JP-A 28521/1986, EP-A 172636). The ring-opening reaction and polymerization (hereafter referred to as ring-opening polymerization) is conducted by a method wherein a cyclic dimer of a lactic acid is used and a catalyst is added while heating (e.g. J. H. R. Woodland et. al.; J. Med. Chem., 16, 897 (1973)).

Although the weight-average molecular weight of a polylactic acid produced by ring-opening polymerization is not especially limited as long as it is larger than the weight-average molecular weight of a polymer of lactic acid which is obtained by hydrolysis (about 25,000 to about 60,000), it ranges, for instance, from about 50,000 to about 200,000, preferably from about 60,000 to about 100,000.

As the polylactic acid produced by ring-opening polymerization, one that is on the market and available to the public can be used.

Hydrolysis of a polylactic acid produced by ring-opening polymerization to obtain a polymer of lactic acid used in the present invention is conducted in the presence of an acid or a base according to a per se known method. Further, the hydrolysis is conducted in the presence of water.

Examples of the acid include inorganic acids such as hydrochloric acid, nitric acid, sulfuric acid and phosphoric acid; and organic acids such as lactic acid, acetic acid, tartaric acid, citric acid and succinic acid. Examples of the base include alkali metal hydroxides such as sodium hydroxide and potassium hydroxide; alkali metal carbonates such as sodium carbonate and potassium carbonate. When hydrolysis is conducted in the presence of a base, release of a physiologically active substance from a sustained-release preparation is sometimes affected depending on the residual base. Therefore, hydrolysis is preferably conducted in the presence of an acid.

Hydrolysis is normally conducted in a solvent which does not interfere with the reaction. Examples of the solvent include alcohols such as methanol, ethanol and propanol; ethers such as tetrahydrofuran, dioxane, diethyl ether and diisopropyl ether; water and mixtures thereof. An excess amount of the above-described acid or base can be employed as a solvent.

Temperature at which hydrolysis is conducted ranges, for instance, from about 0 to about 100° C., preferably from about 10 to about 100° C.

Duration of hydrolysis varies depending on the weight-average molecular weight of the polylactic acid produced by ring-opening polymerization; kinds of the acid or a base used; kinds of the solvent used; temperature and the like. Therefore, it is appropriately decided by collecting a part of a polylactic acid and a polymer of lactic acid in the hydrolysis process and determining the weight-average molecular weight of the collected polylactic acid and a polymer of lactic acid. Duration of hydrolysis is not especially limited but ranges, for instance, from about 1 hour to about 10 days, preferably from about 10 hours to about 5 days.

Although a polylactic acid produced by ring-opening polymerization provides a sustained-release preparation with a large initial burst, the polylactic acid which is hydrolyzed, i.e. the polymer of lactic acid used in the present invention provides a sustained-release preparation with a small initial burst.

A hydrolyzed polylactic acid is preferably subjected to a refining process. The refining process is conducted by dissolving the hydrolyzed polylactic acid in an organic solvent, injecting the thus obtained solution into water or a mixed solution of water and a water-soluble organic solvent, and separating a precipitated polymer of lactic acid.

Examples of the organic solvent include halogenated hydrocarbons such as dichloromethane, chloroform, chloroethane, dichloroethane, trichloroethane and carbon tetrachloride; ketones such as acetone; ethers such as tetrahydrofuran, ethyl ether and isopropyl ether; esters such as ethyl acetate, butyl acetate; aromatic hydrocarbons such as benzene, toluene and xylene. The amount of the organic solvent used ranges, for instance, from about 3 to about 20 times (w/v) relative to the hydrolyzed polylactic acid.

Examples of the water-soluble organic solvent include acetone, methanol, ethanol, tetrahydrofuran and acetonitrile. The amount of the water or mixed solution of water and a water-soluble organic solvent used is not especially limited but normally is a large excess amount relative to the hydrolyzed polylactic acid.

Temperature at which the refining process is conducted ranges normally from about 0 to about 90° C., preferably from about 20 to about 70° C.

The above-described refining process enables elimination of water-soluble low-molecular compounds, for instance, those having the weight-average molecular weight of at most 1,000. Use of a polymer of lactic acid which is subjected to such refining process enables increasing an entrapment ratio of a physiologically active substance in a production process of a sustained-release preparation, and enables production of a sustained-release preparation with a reduced initial burst.

Further, by hydrolyzing and refining a polylactic acid produced by ring-opening polymerization, a polymer of lactic acid is produced which is substantially free from a poisonous catalyst which is used in the ring-opening polymerization and exemplified by zinc compounds such as zinc oxide and tin compounds such as tin (II) octanate.

Examples of the physiologically active substance suitable for use in the present invention include, but are not limited to, physiologically active peptides, antibiotics, antitumor agents, antipyretic agents, analgesics, anti-inflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, antidiabetics, antihyperlipidemic agents, anticoagulants, hemolytics, antituberculosis agents, hormones, narcotic antagonists, bone resorption suppressors, osteogenesis promoters and angiogenesis inhibitors.

The physiologically active peptide is preferably one consisting of 2 or more amino acids and having a molecular weight of about 200 to about 80,000. The physiologically active peptide is preferably LH-RH (luteinizing hormone-releasing hormone) agonists and LH-RH antagonists. Examples of the LH-RH agonists include a peptide represented by the formula:

(Pyr)Glu-R$_1$-Trp-Ser-R$_2$-R$_3$-R$_4$-Arg-Pro-R$_5$     (I)

wherein R$_1$ represents His, Tyr, Trp or p-NH$_2$-Phe; R$_2$ represents Tyr or Phe; R$_3$ represents Gly or an optionally substituted D-type amino acid residue; R$_4$ represents Leu, Ile or Nle; R$_5$ represents Gly-NH-R$_6$ (R$_6$ is hydrogen or an alkyl group with or without hydroxy group) or NH-R$_7$ (R$_7$ is hydrogen, an alkyl group with or without amino or hydroxy group, or ureido (—NH—CO—NH$_2$)); or a salt thereof.

With respect to the formula (I) above, the D-type amino acid residue in R$_3$ is exemplified by α-D-amino acids having up to 9 carbon atoms (e.g., D-Leu, Ile, Nle, Val, Nval, Abu, Phe, Phg, Ser, Thr, Met, Ala, Trp, α-Aibu). The substituent in R$_3$ is exemplified by tert-butyl, tert-butoxy, tert-butoxycarbonyl, methyl, dimethyl, trimethyl, 2-naphthyl, indolyl-3-yl, 2-methyl-indolyl, benzyl-imidazo-2-yl.

In the formula (I), the alkyl group in R$_6$ or R$_7$ is preferably a C$_{1-4}$ alkyl group. Examples of the alkyl group include methyl, ethyl, propyl, isopropyl, butyl, isobutyl, sec-butyl and tert-butyl.

Examples of the salt of peptide (I) [hereafter also referred to as peptide (I)] include acid salts (e.g., carbonate, bicarbonate, acetate, trifluoroacetate, propionate, succinate) and metal complex compounds (e.g., copper complex, zinc complex).

Peptide (I) or a salt thereof can be produced, for example, by a method which is described in U.S. Pat. Nos. 3,853,837, 4,008,209 and 3,972,859, British Patent No. 1,423,083, Proceedings of the National Academy of Science of the United States of America, Vol. 78, pp. 6509–6512 (1981), or an analogous method thereto.

Peptide (I) is preferably one of the following formulae (a) to (j).

(a) leuprorelin [a peptide represented by the formula (I) wherein R$_1$ is His, R$_2$ is Tyr, R$_3$ is D-Leu, R$_4$ is Leu, and R$_5$ is NHCH$_2$—CH$_3$];

(b) Gonadrelin

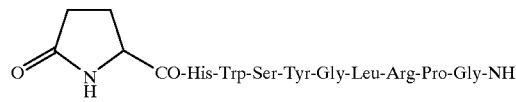

(German Patent No. 2213737); (c) Buserelin

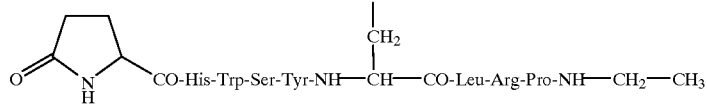

(U.S. Pat. No. 4,024,248, German Patent No. 2438352, Japanese Patent Unexamined Publication No 41359/1976); (d) Triptorelin

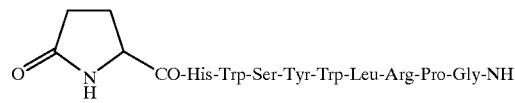

(U.S. Pat. No. 4,010,125, Japanese Patent Unexamined Publication No. 31073/1977); (e) Goserelin

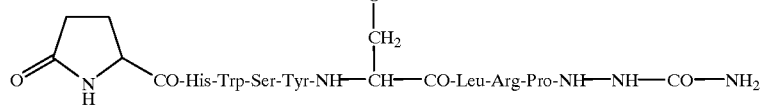

(U.S. Pat. No. 4,100,274, Japanese Patent Unexamined Publication No. 136172/1977); (f) Nafarelin

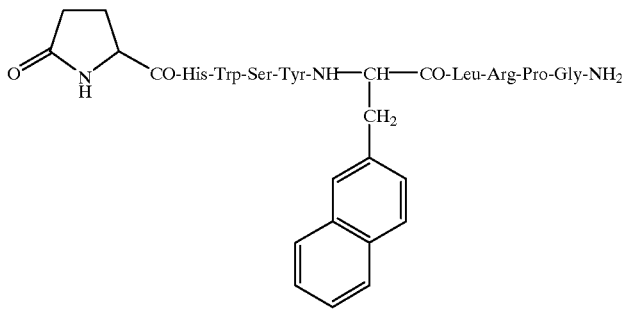

(U.S. Pat. No. 4,234,571, Japanese Patent Unexamined Publication Nos. 164663/1980, 264498/1988 and 25794/1989;

(g) Histrelin

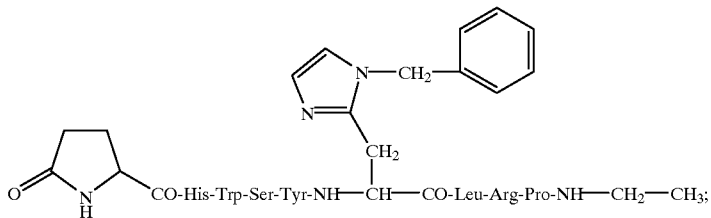

(h) Deslorelin

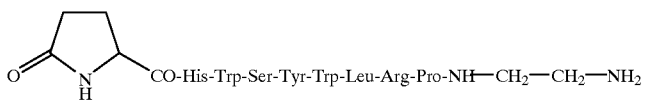

(U.S. Pat. Nos. 4,569,967 and 4,218,439); (i) Meterelin

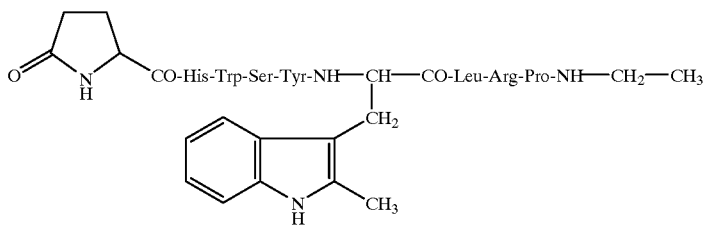

(WO9118016); (j) Lecirelin

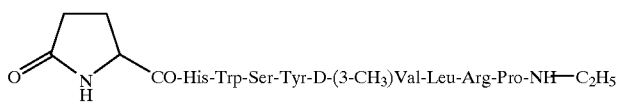

(Belgium Patent No. 897455, Japanese Patent Unexamined Publication No. 59654/1984).

In the above-described formulae (c) to (j), an amino acid which corresponds to $R_3$ in the formula (I) is of D-configuration.

Peptide (I) or a salt thereof is especially preferably leuprorelin or leuprorelin acetate. The leuprorelin acetate is an acetic acid salt of leuprorelin.

Examples of the LH-RH antagonists include those disclosed in U.S. Pat. Nos. 4,086,219, 4,124,577, 4,253,997 and 4,317,815, or a peptide represented by the formula:

(4) NAcD2Nal-D4ClPhe-D3Pal-Ser-Tyr-DhArg(Et$_2$)-Leu-hArg(Et$_2$)-Pro-DAlaNH$_2$•n(CH$_3$COOH)
wherein n represents a real number of 1 to 3.

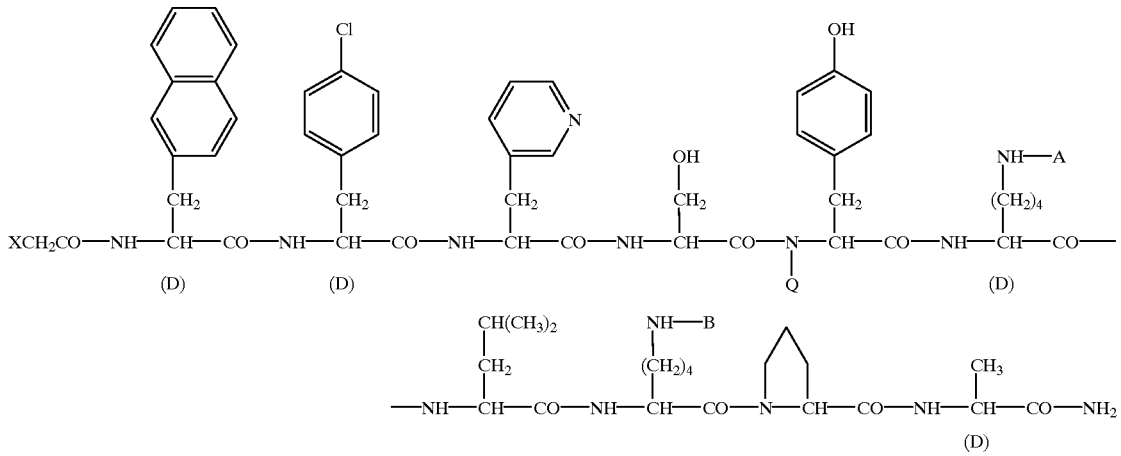
(II)

wherein X represents hydrogen or tetrahydrofurylcarboxamide; Q represents hydrogen or methyl; A represents nicotinoyl or N,N'-diethylamidino; B represents isopropyl or N,N'-diethylamidino; (hereafter also referred to as peptide (II)) or a salt thereof.

With respect to the formula (II), X is preferably tetrahydrofurylcarboxamide, more preferably (2S)-tetrahydrofurylcarboxamide. Also, A is preferably nicotinoyl; B is preferably isopropyl.

When peptide (II) has one or more asymmetric carbon atoms, two or more optical isomers are present. Peptide (II) can be used as such optical isomers or mixtures thereof.

The salt of peptide (II) is preferably a pharmacologically acceptable salt. Such salts include salts formed with inorganic acids (e.g., hydrochloric acid, sulfuric acid, nitric acid), organic acids (e.g., carbonic acid, bicarbonic acid, succinic acid, acetic acid, propionic acid, trifluoroacetic acid) etc. More preferably, the salt of peptide (II) is a salt formed with an organic acid (e.g., carbonic acid, bicarbonic acid, succinic acid, acetic acid, propionic acid, trifluoroacetic acid), with greater preference given to a salt formed with acetic acid. These salts may be mono- through tri-salts.

Preferable examples of peptide (II) or a salt thereof are the following formulae (1) to (4).

The above formulae (2) and (4) show either salts or solvates.

Peptide (II) or a salt thereof is more preferably (1) or (2) above, which are especially preferably S-isomers. Hereafter the S-isomer of the above (1) are referred to as peptide Al.

Peptide (II) or a salt thereof can be produced by per se known methods. Such methods include the methods described in Japanese Patent Unexamined Publication No. 101695/1991 (EP-A 413209) and the Journal of Medicinal Chemistry, Vol. 35, p. 3942 (1992) and other publications, and similar methods.

Examples of physiologically active peptides suitable for use in this invention further include insulin, somatostatin, somatostatin derivative (Sandostatin; see U.S. Pat. Nos. 4,087,390, 4,093,574, 4,100,117 and 4,253,998), growth hormones, prolactin, adrenocorticotropic hormone (ACTH), ACTH derivatives (e.g., ebiratide), melanocyte-stimulating hormone (MSH), thyrotropin-releasing hormone [represented by the structural formula: (Pyr)Glu-His-ProNH$_2$, hereinafter also referred to as TRH] and salts and derivatives thereof (see Japanese Patent Unexamined Publication Nos. 121273/1975 and 116465/1977), thyroid-stimulating hormone (TSH), luteinizing hormone (LH), follicle-stimulating hormone (FSH), vasopressin, vaso- (1)
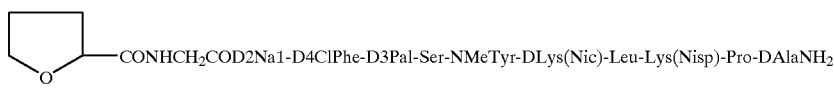

(2)
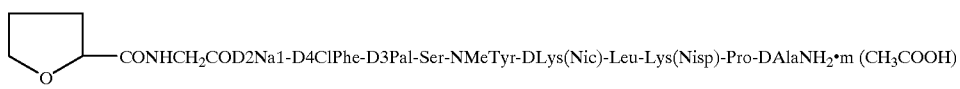

wherein m represents a real number of 1 to 3.

(3) NAcD2Nal-D4ClPhe-D3Pal-Ser-Tyr-DhArg(Et$_2$)-Leu-hArg(Et$_2$)-Pro-DAlaNH$_2$ pressin derivative [desmopressin, see Folia Endocrinologica Japonica, Vol. 54, No. 5, pp. 676–691 (1978)], oxytocin, calcitonin, parathyroid hormone (PTH), glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., α-, β- and γ-interferons), interleukins (e.g., 1, 2, 3, 4, 5, 6, 7, 8, 9, 10, 11 and 12), tuftsin, thymopoietin, thymosin, thymostimulin, thymic humoral factor (THF), blood thymic factor (FTS) and derivative thereof (see U.S. Pat. No. 4,229,438), other thymic factors [Igaku no Ayumi, Vol. 125, No. 10, pp. 835–843 (1983)], tumor necrosis factor (TNF), colony-stimulating factors (e.g., CSF, GCSF, GMCSF, MCSF), motilin, dynorphin, bombesin, neurotensin, caerulein, bradykinin, urokinase, asparaginase, kallikrein, substance P, insulin-like growth factors (IGF-I, IGF-II), nerve growth factor (NGF), cell growth factors (e.g., EGF, TGF-α, TGF-β, PDGF, acidic FGF, basic FGF), bone morphogenic factor (BMP), nerve nutrition factors (e.g., NT-3, NT-4, CNTF, GDNF, BDNF), blood coagulation factors VIII and IX, lysozyme chloride, polymixin B, colistin, gramicidin, bacitracin, erythropoietin (EPO), thrombopoietin (TPO), and endothelin-antagonistic peptides (see European Patent Publication Nos. 436189, 457195 and 496452, and Japanese Patent Unexamined Publication Nos. 94692/1991 and 130299/1991).

Examples of the antibiotics include gentamicin, dibekacin, kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, mochisalactam, thienamycin, sulfazecin and aztreonam.

Examples of the antitumor agents include bleomycin, methotrexate, actinomycin D, mitomycin C, binblastin sulfate, bincrystin sulfate, daunorubicin, adriamycin, neocartinostatin, cytosinearabinoside, fluorouracil, tetrahydrofuryl-5-fluorouracil, krestin, picibanil, lentinan, levamisole, bestatin, azimexon, glycyrrhizin, polyI:C, polyA:U and polyICLC.

Examples of the antipyretic agents, analgesics and anti-inflammatory agents include salicylic acid, sulpyrine, flufenamic acid, diclofenac, indomethacin, morphine, pethidine hydrochloride, levorphanol tartrate and oxymorphone.

Examples of the antitussive expectorants include ephedrine hydrochloride, methylephedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproterenol hydrochloride, sulbutamol sulfate and terbutaline sulfate.

Examples of the sedatives include chlorpromazine, prochlorperazine, trifluoperazine, atropine sulfate and methylscopolamine bromide.

Examples of the muscle relaxants include pridinol methanesulfonate, tubocurarine chloride and pancuronium bromide.

Examples of the antiepileptics include phenytoin, ethosuximide, acetazolamide sodium and chlordiazepoxide.

Examples of the antiulcer agents include metoclopramide and histidine hydrochloride.

Examples of the antidepressants include imipramine, clomipramine, noxiptiline and phenerdine sulfate.

Examples of the anti-allergic agents include diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride.

Examples of the cardiotonics include trans-paioxocamphor, theophyllol, aminophylline and etilefrine hydrochloride.

Examples of the antiarrhythmic agents include propranol, alprenolol, bufetolol and oxprenolol.

Examples of the vasodilators include oxyfedrine hydrochloride, diltiazem, tolazoline hydrochloride, hexobendine and bamethan sulfate.

Examples of the hypotensive diuretics include hexamethonium bromide, pentolinium, mecamylamine hydrochloride, ecarazine hydrochloride and clonidine.

Examples of the antidiabetics include glymidine sodium, glipizide, fenformin hydrochloride, buformin hydrochloride and metformin.

Examples of the antihyperlipidemic agents include pravastatin sodium, simvastatin, clinofibrate, clofibrate, simfibrate and bezafibrate.

Examples of the anticoagulants include heparin sodium.

Examples of the hemolytics include thromboplastin, thrombin, menadione sodium hydrogen sulfite, acetomenaphthone, ε-aminocaproic acid, tranexamic acid, carbazochrome sodium sulfonate and adrenochrome monoaminoguanidine methanesulfonate.

Examples of the antituberculosis agents include isoniazid, ethambutol and p-aminosalicylic acid.

Examples of the hormones include predonizolone, predonizolone sodium phosphate, dexamethasone sodium sulfate, betamethasone sodium phosphate, hexestrol phosphate, hexestrol acetate and methimazole.

Examples of the narcotic antagonists include levallorphan tartrate, nalorphine hydrochloride and naloxone hydrochloride.

Examples of the bone resorption suppressors include ipriflavone, alendronate and risedronate.

Examples of the osteogenesis promoters include polypeptides such as BMP, PTH, TGF-β and IGF-1, and (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide, 2-(3-pyridyl)-ethane-1,1-diphosphonic acid and raloxifene.

Examples of the angiogenesis suppressors include angiogenesis-suppressing steroid [see Science, Vol. 221, p. 719 (1983)], fumagillin (see European Patent Publication No. 325199), fumagillol derivatives (see European Patent Publication Nos. 357061, 359036, 386667 and 415294) and batimastat.

The physiologically active substance may be used as such or as a pharmacologically acceptable salt. Employed are salts formed with inorganic acids such as hydrochloric acid, sulfuric acid and nitric acid, and salts formed with organic acids such as carbonic acid and succinic acid, when the physiologically active substance has a basic group such as an amino group. Employed are salts formed with inorganic bases exemplified by alkali metals such as sodium and potassium, salts formed with organic bases exemplified by organic amines such as triethylamine, and basic amino acids such as arginine, when the physiologically active substance has an acidic group such as a carboxy group.

The physiologically active substance in the sustained-released preparation of the present invention is preferably a physiologically active peptide, more preferably LH-RH agonists or LH-RH antagonists. The physiologically active substance is still more preferably LH-RH agonists, especially preferably the peptide (I) or a salt thereof.

Although the content of physiologically active substance in the sustained-release preparation varies depending on the kind of physiologically active substance used, desired pharmacological action and duration of the action, it ranges, for instance, from about 0.01 to about 50% (w/w), preferably from about 0.1 to about 30% (w/w).

A sustained-release preparation of the present invention is not limited as long as it contains fine particles (i.e., microspheres) comprising a physiologically active substance and a polymer of lactic acid.

Examples of the fine particles (i.e., microspheres) include microcapsules containing one physiologically active substance core in each particle, multiple-core microcapsules containing a large number of physiologically active substance cores in each particle, small particles in which a physiologically active substance in a molecular form is dissolved or dispersed in a polymer of lactic acid as a solid solution, etc.

Preferable examples of a sustained-release preparation of the present invention include a sustained-release preparation, wherein the physiologically active substance is leuprorelin acetate, the polymer of lactic acid has a weight-average molecular weight of about 28,400 to about 47,800, and the preparation releases leuprorelin acetate over a period of at least about 6 months.

A sustained-release preparation of the present invention can be produced by subjecting to microencapsulation a w/o emulsion with a solution containing a physiologically active substance as an internal aqueous phase and with a solution containing a polymer of lactic acid as an oil phase. The microencapsulation is conducted by an in-water drying method, a phase separation method, a spray drying method, or an analogous method thereto.

A w/o emulsion with a solution containing a physiologically active substance as an internal aqueous phase and with a solution containing a polymer of lactic acid of the present invention as an oil phase is produced, for example, as described below.

First, a physiologically active substance is dissolved in water in the concentration of about 0.001 to about 90% (w/w), preferably about 0.01 to about 80% (w/w) to yield an internal aqueous phase. In this internal aqueous phase, a drug-retaining substance exemplified by gelatin, agar, sodium alginate, polyvinyl alcohol or a basic amino acid such as arginine and lysine, may be added for the purpose of increasing an entrapment ratio of the physiologically active substance in the microcapsules. The amount of the drug-retaining substance added is normally about 0.01 to about 100 times by weight, more preferably about 0.05 to about 50 times by weight, the amount of the physiologically active substance. The drug-retaining substance may be previously dissolved to optionally chosen concentrations together with the physiologically active substance and filtered through a sterilizing filter, then freeze-dried and stored, and dissolved freshly before use.

In a sustained-release preparation of the present invention, an entrapment ratio of a physiologically active substance is satisfactory enough even when a drug-retaining substance is not used in an internal aqueous phase.

The internal aqueous phase may be supplemented with a pH regulator for retaining stability or solubility of a physiologically active substance, such as carbonic acid, acetic acid, oxalic acid, citric acid, phosphoric acid, hydrochloric acid, sodium hydroxide, arginine, lysine or a salt thereof. In addition, as stabilizers for the physiologically active substance, albumin, gelatin, trehalose, citric acid, sodium ethylenediaminetetraacetate, dextrin, cyclodextrin (α-, β-, and γ-) and a derivative thereof (e.g., maltosyl β-cyclodextrin, β-cyclodextrin sulfobutyl ether), sodium hydrogen sulfite, polyol compounds such as polyethylene glycol, surfactants such as polyoxyethylene sorbtitan fatty acid esters (e.g. Tween 80, Tween 60; Kao, Japan) and polyoxyethylene castor oil derivatives (e.g. HCO-60, HCO-70; Nikko Chemicals, Japan), p-oxybenzoates (e.g., methyl paraben, propyl paraben), benzyl alcohol, chlorobutanol, thimerosal, etc., may be added.

An internal aqueous phase thus obtained and a solution (oil phase) containing a polymer of lactic acid are mixed to obtain a mixture, which is then subjected to emulsification to yield a w/o emulsion.

As the solution (oil phase) containing a polymer of lactic acid, a solution may be employed that is prepared by dissolving the polymer of lactic acid in an organic solvent. Any organic solvent serves this purpose, as long as it has a boiling point not higher than about 120° C., is hydrophobic and dissolves a polymer of lactic acid. Examples of such organic solvent include halogenated hydrocarbons (e.g., dichloromethane, chloroform, chloroethane, dichloroethane, trichloroethane, carbon tetrachloride), fatty acid esters (e.g., ethyl acetate, butyl acetate), ethers (e.g., ethyl ether, isopropyl ether) and aromatic hydrocarbons (e.g., benzene, toluene, xylene). Two or more of these organic solvents may be used in combination at appropriate ratios. The organic solvent is preferably halogenated hydrocarbons, especially preferably dichloromethane.

Although varying depending on the kind and molecular weight of the polymer of lactic acid and the kind of organic solvent used, the polymer concentration in the organic solvent solution is normally about 0.01 to about 90% (w/w), preferably about 0.1 to about 80% (w/w).

For the purpose of changing compatibility with an internal aqueous phase, distribution of an organic solvent into an external aqueous phase, volatilization and the like, a hydrophilic organic solvent such as ethanol, acetonitrile, acetone and tetrahydrofuran may be added in an oil phase partially. Further, for the purpose of dissolution or stabilization of an internal physiologically active substance, surfactants such as sucrose fatty acid esters may be added. An oil phase thus obtained is normally used after sterilizing or dust-cleaning filtration with a filter. Although depending on stability of a polymer of lactic acid, a solution containing a polymer of lactic acid may be stored in a closed container at room temperature or in a cold place.

The mixing ratio of an aqueous solution containing a physiologically active substance and an organic solvent solution containing a polymer of lactic acid is normally about 0.1 to about 1000 parts by weight, preferably about 1 to about 100 parts by weight of the latter per part by weight of the former. Although varying depending on the kind of physiologically active substance used, desired pharmacological action, duration of action and other factors, the ratio of the physiologically active substance to polymer of lactic acid is normally about 0.01 to about 50% (w/w), preferably about 0.5 to about 40% (w/w), and especially preferably about 0.1 to about 30% (w/w).

An emulsification process is achieved by a known dispersing method, such as an intermittent shaking method, a method using a mechanical stirrer such as a propeller stirrer and a turbine stirrer, a colloidal mill method, a homogenizer method and an ultrasonication method.

Regarding this w/o emulsion, release of a physiologically active substance is affected by degree of emulsification in the emulsion. When the degree of emulsification is insufficient, an initial burst tends to become larger. When an internal aqueous phase is finer beyond a certain extent, an interaction between a physiologically active substance and a polymer of lactic acid becomes stronger and a release control by a polymer of lactic acid depends on biodegradability of the polymer of lactic acid to make a long-term release control more accurate, which is preferable.

Next, the w/o emulsion thus obtained is subjected to microencapsulation process.

For instance, when microencapsulation is conducted by an in-water drying method, said w/o emulsion is further added to another aqueous phase (hereafter referred to as an external aqueous phase) to yield a w/o/w emulsion, followed by removing an organic solvent in an oil phase, to yield microcapsules.

An emulsifier may be added to the above-described external aqueous phase. Any emulsifier can be used, as long as it generally produces a stable o/w emulsion. Examples of such emulsifiers include anionic surfactants (e.g., sodium oleate, sodium stearate, sodium lauryl sulfate), nonionic surfactants (e.g., Tween 80, Tween 60, HCO-60, HCO-70), polyvinyl alcohol, polyvinylpyrrolidone and gelatin. Two or more of these emulsifiers may be used in combination in an appropriate ratio. The emulsifier concentration in an external aqueous phase ranges for instance from about 0.01 to about 20%, preferably from about 0.05 to about 10%.

Removal of an organic solvent can be achieved by known methods, including the method in which the solvent is removed under normal or gradually reduced pressure during stirring using a propeller stirrer, magnetic stirrer or the like, and the method in which the solvent is removed while the degree of vacuum and temperature are adjusted using a rotary evaporator or the like.

The thus-obtained microcapsules are centrifuged or filtered to separate them, and subsequently washed with distilled water several times repeatedly to remove the free physiologically active substance, drug-retaining substance, emulsifier etc. adhering to the microcapsule surface. Then, washed microcapsules are dried under reduced pressure or freeze-dried after redispersion in distilled water to further remove an organic solvent.

For producing microspheres by the phase separation method, a coacervating agent is gradually added to a w/o emulsion while the emulsion is stirred, to precipitate and solidify a polymer of lactic acid. Any coacervating agent can be used, as long as it is a polymeric, mineral oil or vegetable oil compound miscible with the solvent for a polymer of lactic acid and that does not dissolve a polymer of lactic acid for capsulation. Examples of such coacervating agents include silicon oil, sesame oil, soybean oil, corn oil, cotton seed oil, coconut oil, linseed oil, mineral oil, n-hexane and n-heptane. Two or more of these may be used in combination. The amount of the coacervating agents used is, for instance, about 0.01 to about 1,000 times by volume, preferably about 0.1 to about 200 times by volume, relative to a w/o emulsion.

The thus-obtained microspheres are centrifuged or filtered to separate them, after which they are repeatedly washed with a wash such as hexane and heptane to remove the coacervating agent. Then the wash is evaporated by heating or decompression.

If necessary, in the same manner as with the above-described in-water drying method, a free physiologically active substance and an organic solvent are removed.

For producing microcapsules by the spray drying method, a w/o emulsion or a w/o/w emulsion produced in the same manner as in an in-water drying method is sprayed via a nozzle into the drying chamber of a spray drier to volatilize an organic solvent and water in the fine droplets in a very short time, to yield fine microcapsules. Examples of the nozzle include, for instance, a two-fluid nozzle type, a pressure nozzle type and a rotary disc type.

If necessary, microcapsules thus obtained are washed with distilled water several times repeatedly to remove a free physiologically active substance, a drug-retaining substance, an emulsifer, etc. adhering to the microcapsule surface. Then, washed microcapsules may be dried under reduced pressure or freeze-dried after redispersion in distilled water to further remove an organic solvent.

Also, when a physiologically active substance dissolves 1) in an oil phase consisting of one hydrophobic organic solvent (e.g., dichloromethane, chloroform, dichloroethane, carbon tetrachloride, ethyl acetate, cyclohexane) and at least one hydrophobic organic solvent (e.g., methanol, ethanol, acetonitrile), or 2) in an oil phase consisting of a polymer solution in a hydrophobic organic solvent, or 3) in an oil phase prepared by adding at least one surfactant (e.g., glycerol fatty acid ester, propylene glycol fatty acid ester, sucrose fatty acid ester) to the above-described hydrophobic organic solvent; these oil phases may be dispersed in an external aqueous phase used in the above-described in-water drying method to yield an o/w emulsion, followed by removing an organic solvent in the oil phase in the same manner as in the above-described in-water drying method, to yield microcapsules. Further, this o/w emulsion can be subjected to the above-described phase separation method or spray drying method to prepare microcapsules.

The sustained-release preparation of the present invention preferably comprises an excipient. The excipient is desired to be low in toxicity when administered to a living body; be easy to dry by freeze-drying or spray-drying; and dissolve rapidly when administered to a living body or dissolve at the time of use. Examples of such excipient includes, for instance, sugars, cellulose derivatives, amino acids, proteins, polyacrylic acid derivatives, organic salts and inorganic salts. Two or more of these excipients may be used in combination in an appropriate ratio.

Examples of the sugars include D-mannitol, sodium alginate, fructose, dextran, dextrin, sucrose, D-sorbitol, lactose, glucose, maltose, starches and trehalose.

Examples of the cellulose derivatives include carboxymethylcellulose, hydroxypropylmethylcellulose, ethylcellulose, hydroxymethylcellulose, hydroxypropylcellulose, cellulose acetate phthalate, hydroxypropylmethylcellulose phthalate and hydroxymethylcellulose acetate succinate.

Examples of the amino acids include glycine, alanine, tyrosine, arginine and lysine.

Examples of the proteins include gelatin, fibrin, collagen and albumin.

Examples of the polyacrylic acid derivatives include sodium polyacrylic acid, methacrylic acid/acrylic acid copolymer (Eudragit, produced by Rohm Company, Germany).

Examples of the organic salts include sodium citrate, sodium tartrate, sodium carbonate and potassium carbonate.

Examples of the inorganic salts include sodium chloride, potassium chloride, sodium phosphate and potassium phosphate.

In addition to the above-described examples, water-soluble polymers which do not dissolve a polymer used as a base for a sustained-release preparation, such as polyvinyl pyrrolidone and polyvinyl alcohol can also be used as an excipient. The excipient is preferably sugar, most preferably D-mannitol, which is easy to freeze-dry and low in toxicity.

The amount of an excipient used is determined by solubility of an excipient, isotonicity, viscosity, dispersibility and stability of a solution obtained by dissolving an excipient. When a sustained-release preparation is dried, the excipient content in a dried sustained-release preparation is, for instance, about 0.5 to about 99% (w/w), preferably about 1 to about 90% (w/w), more preferably about 2 to about 60% (w/w). When D-mannitol is used as an excipient, the excipient content in a dried sustained-release preparation is especially preferably about 2 to about 40% (w/w).

Addition of these excipients brings excellent effects such as 1) frequency of contact and impact between particles during drying or after drying of a sustained-release preparation (especially microspheres) are lowered to keep uniformity of particles during freeze-drying or spray drying; 2) drying of a sustained-release preparation at a temperature higher than a glass transition temperature is possible to remove water or an organic solvent more perfectly; 3) stability of a sustained-release preparation with the passage of time is improved to yield a sustained-release preparation having good dispersibility, being not limited to storage in a cool place, and having a long-term validity for use, for instance, at room temperature.

In the present invention, a sustained-release preparation comprising an excipient is produced by, for instance, admixing with an excipient microcapsules obtained by the above-described in-water drying method, phase separation method or spray drying method. The microcapsules may be those dried under reduced pressure after washing, or those freeze-dried after washing and then redispersed in distilled water. A method of admixing is not especially limited, and, for instance, a mechanical mixer is employed. Preferably, a method which brings a homogeneous mixture is employed.

Also, a sustained-release preparation comprising an excipient is produced by spraying an aqueous solution of an excipient from another nozzle together with spraying a w/o emulsion when microcapsules are produced by a spray drying method.

Further, a sustained-release preparation comprising an excipient is produced by employing an aqueous solution of an excipient as an external aqueous phase when a w/o/w emulsion used in an in-water drying method or a spray drying method is produced.

A sustained-release preparation comprising an excipient is preferably produced by washing microcapsules obtained by an in-water drying method, a phase separation method or a spray drying method; dispersing washed microcapsules in distilled water in which an excipient is dissolved or suspended; and then freeze-drying or drying under reduced pressure. Also, freeze-drying or drying under reduced pressure may be conducted after an excipient is dissolved or suspended in dispersion which is obtained by dispersing washed microcapsules in distilled water. Especially, a homogeneous mixture is obtained by freeze-drying after dispersing washed microcapsules in distilled water solution of an excipient, or dissolving an excipient in a dispersion obtained by dispersing washed microcapsules in distilled water.

If necessary, microcapsules obtained by the above-described in-water drying method, phase separation method or spray drying method are heated to a temperature not lower than a glass transition temperature (Tg) of a polymer employed as a base and not so high as to cause aggregation of each microcapsule particles, to remove water and an organic solvent more perfectly and improve a sustained release property. In this case, the organic solvent is preferably removed to the extent of less than about 1,000 ppm, preferably less than about 500 ppm, more preferably less than 100 ppm.

The glass transition temperature is defined as the intermediate glass transition point obtained using a differential scanning calorimeter (DSC) when the temperature is increased at a rate of 10 or 20° C. per minute.

The heating is preferably conducted after microcapsules are freeze-dried or dried under reduced pressure after an optional addition of an excipient. However, the timing of heating is not especially limited, and it may be, for instance, after subdivision.

If the heating temperature is below a glass transition temperature of a polymer employed as a base, removal of water or an organic solvent is sometimes insufficient. Conversely, if the heating temperature is too high, a risk of aggregation and deformation of microcapsules, and decomposition or degradation of a physiologically active substance is increased. The heating temperature can not be specified in general terms but can be appropriately determined in consideration of physical properties (e.g., molecular weight, stability) of a polymer employed as a base, a physiologically active substance, mean particle diameter of microcapsules, heating time, degree of desiccation of microcapsules, heating method and the like.

The heating temperature preferably ranges from a glass transition temperature of a polymer employed as a base to temperature which is about 30° C. higher than the glass transition temperature, more preferably from a glass transition temperature of the polymer to temperature which is about 20° C. higher than the glass transition temperature.

The heating time is also dependent on the heating temperature, the amount of treated microcapsules and the like. Generally, however, it is about 6 to about 120 hours, more preferably about 12 to about 96 hours, after microcapsules themselves have reached a specific temperature. Although the upper limit of the heating time is not especially limited as long as the residual organic solvent or water is not more than a permissible amount, it is preferable that heating is finished immediately after the residual organic solvent or water gets not more than a permissible amount since microcapsules are softened and then deformed because of a physical contact between microcapsules or a load of accumulated microcapsules under the temperature conditions of not lower than a glass transition temperature.

The heating method is not especially limited as long as a method by which microcapsules are uniformly heated is employed. Preferable examples of the heating method include a method in which heating and drying is conducted under reduced pressure by using a freeze-drying machine or a decompression constant temperature machine.

A sustained-release preparation of the present invention may be any of injectable preparations, implants, oral preparations (e.g., powders, granules, capsules, tablets, syrups, emulsions, suspensions), nasal preparations or suppositories (e.g., rectal suppositories, vaginal suppositories).

These preparations can be produced by known methods in common use for pharmaceutical production.

For example, an injectable preparation is prepared by dispersing the above-described microcapsules in an aqueous dispersant or an oily dispersant.

Examples of the aqueous dispersant include a solution which is prepared by dissolving in distilled water an isotonizing agent (e.g., sodium chloride, glucose, D-mannitol, sorbitol, glycerol), a dispersing agent (e.g, Tween 80, HCO-50, HCO-60, carboxymethylcellulose, sodium alginate), a preservative (e.g., benzyl alcohol, benzalkonium chloride, phenol), a soothing agent (e.g., glucose, calcium gluconate, procaine hydrochloride) etc. Examples of the oily dispersant include olive oil, sesame oil, peanut oil, soybean oil, corn oil, and middle-chain fatty acid glycerides.

The injectable preparation may be loaded into a chamber of a pre-filled syringe. Also, dispersants and microcapsules may be loaded separately into a different chamber of so-called Double-Chamber Pre-filled Syringe (DPS).

In a process of preparing an injectable preparation, a more stable sustained-release injectable preparation is obtained by adding to microcapsules an excipient (e.g., mannitol, sorbitol, lactose, glucose) in addition to the above-described ingredients, redispersing, solidifying by freeze-drying or spray drying, and then adding distilled water for injection or an appropriate dispersant at the time of use.

An oral preparation can be produced by, for example, adding an excipient (e.g., lactose, sucrose, starch), a disintegrating agent (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethylene glycol 6000) to the above-described microcapsules, subjecting the mixture to compressive shaping, followed by coating to mask the taste or confer an enteric or sustained-release property by a per se known method when necessary. Examples of coating agents include hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rohm Company, Germany, methacrylic acid-acrylic acid copolymer), and dyes such as titanium oxide and red iron oxide.

A nasal preparation may be solid, semi-solid or liquid. For example, a solid nasal preparation can be produced normally by adding an excipient (e.g., glucose, mannitol, starch, microcrystalline cellulose), a thickening agent (e.g., natural rubber, cellulose derivative, acrylic acid polymer) etc. to the above-described microcapsules and mixing them, although microcapsules as such may be used. A liquid nasal preparation can be produced in almost the same manner as for the above-described injectable preparation. All these nasal preparations may contain a pH regulator (e.g., carbonic acid, phosphoric acid, citric acid, hydrochloric acid, sodium hydroxide), an antiseptic (e.g., p-oxybenzoate, chlorobutanol, benzalkonium chloride) etc.

A suppository may be oily or aqueous; and solid, semi-solid or liquid. The suppository is produced normally by using oily bases, aqueous bases or aqueous gel bases. Examples of the oily bases include glycerides of higher fatty acids [e.g., cacao fat, Witepsol-series products (Dynamite Nobel Company, Germany)], moderate fatty acids [e.g., MIGLYOL-series products (Dynamite Nobel Company, Germany)], and vegetable oils (e.g., sesame oil, soybean oil, cottonseed oil). Examples of the aqueous bases include polyethylene glycols and propylene glycol. Examples of the aqueous gel bases include natural rubbers, cellulose derivatives, vinyl polymers and acrylic acid polymers.

A sustained-release preparation of the present invention is preferably used in the form of an injectable preparation.

The particle diameter of fine particles such as microcapsules in an injectable preparation is chosen over the range in which the requirements concerning the dispersibility and needle passability are met when a sustained-release preparation of the present invention is an injectable preparation. For example, mean diameter falls within the range from about 1 to about 300 µm, preferably about 5 to about 100 µm.

A sustained-release preparation of the present invention is of low toxicity and can be administered safely to mammals (e.g., mice, rats, dogs, cats, sheep, swine, horses, bovines, monkeys, humans).

Although varying depending on the kind and content of the physiologically active substance, duration of a physiologically active substance release, subject species, and purpose of administration, the dose of a sustained-release preparation may be set at any level, as long as the active ingredient is effective. When a sustained-release preparation of the present invention is administered to humans, the dose of the preparation per administration can be chosen as appropriate over the range from about 1 mg to about 10 g, preferably from about 10 mg to about 2 g per adult (weight 50 kg). When the sustained-release preparation is an injectable preparation, the volume of a suspension can be chosen as appropriate over the range from about 0.1 to about 5 ml, preferably from about 0.5 to about 3 ml.

Especially, when a physiologically active substance is leuprorelin or leuprorelin acetate, a sustained-release preparation of the present invention is useful for hormone-dependent diseases such as prostatic cancer, prostatic hypertrophy, breast cancer, endometriosis, myoma of the uterus, and neurogenic precocious puberty, and contraception.

The dose of the sustained-release preparation per administration for one month in terms of a physiologically active substance ranges, for instance, from about 1.88 to about 7.5 mg per adult (body weight 50 kg). For instance, in a sustained-release preparation intended for 6 months release, the dose of leuprorelin or leuprorelin acetate per administration ranges from about 11.3 to about 45 mg, the dose of the sustained-release preparation per administration ranges from about 75 to about 800 mg.

When a sustained-release preparation of the present invention is administered to a domestic animal (e.g., dogs, cats, sheep, swine, horses, bovines, monkeys) for the purpose of contraception or softening of meat, the dose of the preparation is set by determining clearance of a subject animal species. For instance, the subject animal species is a dog, the dose of a sustained-release preparation per administration for one month in terms of a physiologically active substance ranges, for instance, from about 0.03 to about 1.5 mg/kg. For instance, in a sustained-release preparation intended for 6 months release, the dose of a physiologically active substance per administration ranges from about 0.18 to about 9 mg/kg, the dose of the sustained-release preparation per administration ranges from about 1.2 to about 200 mg/kg.

The present invention is hereinafter described in more detail by means of the following Reference Examples, Examples, Comparative Examples and Experimental Examples, which are not to be construed as limitative, as long as they fall within the scope of the present invention. Unless otherwise specified, % (percent) below means % by weight.

REFERENCE EXAMPLE 1

10 g of DL-polylactic acid having a weight-average molecular weight of 79,900 which is produced by ring-opening polymerization (RESORMER, R206, Lot No. 211967, produced by Boehringer Ingelheim, Germany) (hereafter referred to as Polymer F) was hydrolyzed by soaking it in 400 ml of a solution wherein DL-lactic acid was diluted with distilled water 1/50 or 1/100 (w/w) times (respectively pH 2.09, pH 2.27) at 60° C.

Next, the hydrolyzed polylactic acid was collected from the resultant mixture, which was dissolved in 500 ml of dichloromethane respectively and then washed three times with 1,000 ml of distilled water for 30 minutes respectively to remove water-soluble oligomers. An organic solvent phase was laid on glass laboratory dishes to evaporate dichloromethane, and then dried for one day at 40° C. under reduced pressure. Before the organic solvent phase were solidified completely, polymer of lactic acid was foamed by adjusting the degree of vacuum to enlarge the volume of the polymer of lactic acid and then promote evaporation of dichloromethane. The foamed substance obtained was pulverized to yield polymers shown in Table 1.

TABLE 1

| Lactic acid conc. (w/w) | Hydrolyzation time (day) | Weight-average molecular weight | Yield (%) | Polymer |
|---|---|---|---|---|
| 1/50 | 2 | 47,800 | 96.6 | A |
| 1/100 | 3 | 31,200 | 82.7 | B |
| 1/50 | 3 | 28,400 | 96.0 | C |

REFERENCE EXAMPLE 2

In the same manner as in Reference Example 1, Polymer F was hydrolyzed to yield polymers shown in Table 2.

TABLE 2

| Lactic acid conc. (w/w) | Hydrolyzation time (day) | Weight-average molecular weight | Yield (%) | Polymer |
|---|---|---|---|---|
| 1/50 | 1.1 | 69,200 | 59.3 | D |
| 1/50 | 1.2 | 62,300 | — | E |

EXAMPLE 1

Microspheres shown in Table 3 were produced by an in-water drying method using various polymers obtained in Reference Example 1.

Namely, 550 mg of leuprorelin acetate was dissolved in 1 ml of distilled water. To the obtained solution was added a solution wherein 4 g of a polymer produced in Reference Example 1 was dissolved in dichloromethane, which was subjected to emulsification under stirring for about one minute with a small-size homogenizer (Polytron, produced by Kinematica, Switzerland) to yield a w/o emulsion. This w/o emulsion was cooled to 13° C., which was added to 1,000 ml of a 0.25% polyvinyl alcohol (PVA) aqueous solution previously cooled at the same temperature, followed by emulsification with a homomixer (Tokusyu Kika, Japan) (rotation rate: about 7,000 rpm) to yield a w/o/w emulsion. This w/o/w emulsion was gently stirred for about 3 hours to remove solvents. The obtained microspheres were sieved with a 74 μm sieve to remove coarse particles and then collected by centrifugation. The obtained precipitate was washed three times with distilled water to remove a free drug and PVA, which was freeze-dried after redispersion with a small amount of water.

TABLE 3

| Polymer | Dichloromethane amount (ml) | Cooling temperature (° C.) | Yield (%) | Microsphere |
|---|---|---|---|---|
| A | 10.0 | 13 | 86.6 | A |
| B | 10.0 | 13 | 87.5 | B |

COMPARATIVE EXAMPLE 1

In the same manner as in Example 1, microspheres shown in Table 4 were produced using Polymer D and E produced in Reference Example 2, DL-polylactic acid having a weight-average molecular weight of 22,200 (RESOMER, R203, Lot No. 15004, produced by Boehringer Ingelheim, Germany) (hereafter referred to as Polymer G), DL-polylactic acid having a weight-average molecular weight of 47,200 (PL-50000, produced by Taki Kagaku, Japan) (hereafter referred to as Polymer H), and a polymer which is obtained by washing Polymer H with water (hereafter referred to as Polymer H').

TABLE 4

| Polymer | Dichloromethane amount (ml) | Cooling temperature (° C.) | Yield (%) | Microsphere |
|---|---|---|---|---|
| D | 12.5 | 14 | 73.4 | D |
| E | 12.5 | 13 | 66.6 | E |
| G | 7.5 | 10 | 78.2 | G |
| H | 10.0 | 10 | 65.7 | H |
| H' | 10.0 | 10 | 69.2 | H' |

EXAMPLE 2

6 g of leuprorelin acetate is dissolved in 10 ml of distilled water. To the obtained solution is added 190 g of a solution which is prepared by dissolving in dichloromethane 44 g of Polymer B produced in Reference Example 1 and then filtering, which is subjected to emulsification under stirring for about 8 minutes with an autominimixer (rotation rate: 6,000 rpm) to yield a w/o emulsion. This w/o emulsion is cooled to about 13° C., which is added to 12 L of a 0.1% PVA aqueous solution previously cooled at the same temperature, followed by emulsification with a homomiclineflow (Tokusyu Kika, Japan)(rotation rate: about 7,000 rpm) to yield a w/o/w emulsion. This w/o/w emulsion is gently stirred for about 3 hours to remove solvents. The obtained microspheres are collected and washed in the same manner as in Example 1, followed by redispersion with a small amount of water. 6.4 g of D-mannitol is dissolved in the obtained dispersion, which is sieved and freeze-dried. A rack temperature while drying is gradually increased and drying is conducted finally at 53° C. for 48 hours. The obtained dry preparation is sieved and pulverized to yield microsphere powders. This operation yields about 48 g of microsphere powders containing about 15% of mannitol.

EXAMPLE 3

4 g of peptide Al acetate is dissolved in 6 ml of distilled water. To the obtained solution is added 110 g of a solution which is prepared by dissolving in dichloromethane 30 g of Polymer B produced in Reference Example 1 and then filtering, which is subjected to stirring emulsification for about 5 minutes with an autominimixer (rotation rate: 6,000 rpm) to yield a w/o emulsion. This w/o emulsion is cooled to about 13° C., which is added to 7 L of a 0.1% PVA aqueous solution previously cooled at the same temperature. Then, the same procedure in Example 2 except that the amount of D-mannitol is changed to 4.3 g is conducted to yield microsphere powders. This operation yields about 33 g of microsphere powders containing about 15% of mannitol.

EXAMPLE 4

7.5 g of somatostatin is dissolved in 13 ml of distilled water. To the obtained solution is added a solution which is prepared by dissolving in 250 ml of dichloromethane 100 g of Polymer A produced in Reference Example 1 and then filtering, which is subjected to stirring emulsification for about 5 minutes with an autominimixer (rotation rate: 6,000 rpm) to yield a w/o emulsion. This w/o emulsion is cooled to about 14° C., which is added to 25 L of a 0.1% PVA aqueous solution previously cooled at the same temperature. Then, the same procedure in Example 2 except that a drying condition is changed to finally at 54° C. for 24 hours is conducted to yield microsphere powders. This operation yields about 100 g of microsphere powders containing about 15% of mannitol.

EXAMPLE 5

2 g of h-GH (human growth hormone) and 2 g of arginine are dissolved in 5 ml of distilled water. To the obtained solution is added a solution which is prepared by dissolving in 96 g of dichloromethane 30 g of Polymer B produced in Reference Example 1 and then filtering, which is subjected to emulsification under stirring for about 5 minutes with an autominimixer (rotation rate; 6,000 rpm) to yield a w/o emulsion. This w/o emulsion is cooled to about 13° C., which is added to 3 L of a 0.1% PVA aqueous solution previously cooled at the same temperature. Then, the same procedure in Example 2 except that the amount of D-mannitol is changed to 4 g and that a drying condition is changed to finally at 52° C. for 24 hours is conducted to yield microsphere powders. This operation yields about 30 g of microsphere powders containing about 15% of mannitol.

EXAMPLE 6

Microspheres produced in Example 1 (2.97 mg as a drug) were dispersed in a 0.5 ml of dispersion medium (an aqueous solution containing 1% carboxymethylcellulose sodium, 0.5% Tween 80) to produce an injectable preparation.

COMPARATIVE EXAMPLE 2

Microspheres produced in Comparative Example 1 (2.97 mg as a drug) were dispersed in a 0.5 ml of dispersion medium (an aqueous solution containing 1% carboxymethylcellulose sodium, 0.5% Tween 80) to produce an injectable preparation.

EXPERIMENTAL EXAMPLE 1

Water-soluble oligomer (free acid) contents in polymers produced in Reference Example 1 and polylactic acid on the market (polylactic acid which is produced by ring-opening polymerization and not subjected to hydrolyzation) were determined. As the polylactic acid on the market, Polymer F used in Reference Example 1 and Polymers G and H used in Comparative Example 1 were employed.

Determination of free acid contents were conducted by weighing accurately about 150 mg of each polymer, dissolving it in 5 ml of dichloromethane, shaking and extracting the obtained solution with 10 ml of distilled water for 10 minutes, centrifugalizing the obtained mixture for 8 minutes at 3,000 rpm, sampling 2.5 ml of the obtained aqueous phase, titrating the aqueous phase with a 1 mM aqueous solution of sodium hydroxide using phenol red as an indicator. The results are shown in Table 5.

It is known that free acid contents in a polymer is an important factor affecting an initial burst of a drug and stability of a polymer and that an initial burst via an aqueous channel caused by a free acid, namely "a tunnel effect" is remarkable when a free acid is not less than 0.1% (Pharmaceutical Research, 11, (8) 1143–1147 (1994)).

TABLE 5

| Polymer | A | B | C | F | G | H |
|---|---|---|---|---|---|---|
| Free acid contents (%) | 0.026 | 0.025 | 0.025 | 0.043 | 0.059 | 0.035 |

As is clear from Table 5, free acid contents in polymers obtained in Reference Example 1 showed lower values than free acid contents in polylactic acid on the market.

EXPERIMENTAL EXAMPLE 2

Glass transition temperatures (Tg) of Polymers A to H and H' were determined. The results are shown in Table 6.

TABLE 6

| Polymer | A | B | C | D | E | F | G | H | H' |
|---|---|---|---|---|---|---|---|---|---|
| Glass transition temperature (° C.) | 47.4 | 47.3 | 44.0 | 49.7 | 36.6 | 50.5 | 43.3 | 41.4 | 39.5 |

EXPERIMENTAL EXAMPLE 3

Glass transition temperatures (Tg), drug contents and entrapment ratios of microspheres produced in Example 1 and Comparative Example 1 were determined. The results are shown in Table 7.

TABLE 7

| Microsphere | Glass transition temperature (° C.) | Drug content (%) | Entrapment ratio (%) |
|---|---|---|---|
| A | 52.0 | 11.3 | 93.5 |
| B | 51.4 | 11.3 | 93.5 |
| D | 52.4 | 10.1 | 83.6 |
| E | 52.3 | 11.1 | 91.8 |
| G | 47.3 | 9.7 | 80.2 |
| H | 49.6 | 7.7 | 63.7 |
| H' | 50.0 | 8.4 | 69.5 |

As is clear from Table 7, microspheres produced by using polymers wherein polylactic acid produced by ring-opening polymerization is not hydrolyzed (Polymers G and H) and a polymer which is obtained by washing Polymer H (Polymer H') (Microspheres G, H and H') showed low drug contents and entrapment ratios. Also, as is clear from the above-described Tables 3 and 4, yields of these microspheres were low.

Further, microspheres produced by using a polymer having a molecular weight of more than 60,000 among polymers wherein polylactic acid produced by ring-opening polymerization was hydrolyzed (Polymers D and E) (Microspheres D and E) showed relatively low entrapment ratio. Also, as is clear from the above described Tables 3 and 4, yields of these microspheres were low.

In polymers wherein hydrolyzation is not conducted, there exist a large number of cyclic polymers and a small number of polylactic acid having a terminal carboxyl group. Therefore, in microspheres produced by using such polymers, an entrapment ratio is considered to decrease since interaction between a polymer and a drug is weak, and an entrapment effect of drug particles by a polymer is small.

Further, when a molecular weight of a polymer increases, the ratio of hydrophilic carboxyl groups to hydrophobic groups in a polymer decrease. Therefore, also in microspheres produced by using such a polymer, an entrapment effect of drug particles by a polymer gets smaller, and an entrapment ratio is considered to decrease.

Therefore, in order to incorporate a drug in microspheres preferably, the presence of carboxyl groups having a suitable ratio to hydrophobic alkyl groups is considered to be necessary in a terminal of a polymer chain.

EXPERIMENTAL EXAMPLE 4

The injectable preparation produced in Example 6 and Comparative Example 2 was administered to rats subcutaneously [dose: 2.97 mg/rat (30 µg/kg/day) as a drug, n=5]. Then a drug (leuprorelin acetate) remaining subcutaneously was determined with the passage of time to evaluate drug-release properties. The results are shown in Table 8.

TABLE 8

| Time (week) | Drug remaining ratio (%) ± standard error | | | |
|---|---|---|---|---|
| | Microsphere A | Microsphere B | Microsphere D | Microsphere E |
| 0.000 | 100.0 | 100.0 | 100.0 | 100.0 |
| 0.143 | 82.5 ± 0.5 | 90.9 ± 0.6 | 58.7 ± 2.0 | 56.4 ± 1.0 |
| 1.000 | 81.5 ± 1.1 | 84.8 ± 0.6 | 55.3 ± 0.6 | 55.0 ± 0.4 |
| 4.000 | 62.3 ± 0.8 | 84.7 ± 1.3 | 50.1 ± 0.9 | — |
| 8.000 | 56.6 ± 0.9 | 75.2 ± 0.8 | 26.3 ± 3.5 | 39.7 ± 1.9 |
| 13.000 | 48.4 ± 2.7 | 53.7 ± 1.8 | 21.9 ± 1.8 | 21.0 ± 1.9 |
| 17.000 | 34.2 ± 1.3 | 38.8 ± 1.4 | 12.7 ± 0.5 | 9.9 ± 1.1 |
| 21.000 | 33.3 ± 2.5 | 31.7 ± 2.0 | 9.5 ± 1.9 | 8.5 ± 1.6 |
| 26.000 | 20.2 ± 0.8 | 17.0 ± 0.8 | 9.1 ± 1.1 | — |
| 30.000 | 17.3 ± 1.1 | 6.9 ± 0.5 | — | — |

As is clear from Table 8, microspheres of the present invention (Microspheres A and B) showed a small initial burst and subsequently an almost continuous zero order release of a drug over a long period of about 6 months. On the contrary, Microspherers D and E released almost whole amount of a drug at 17 weeks and showed substantially no subsequent release as well as showing a large initial burst, although polylactic acid having a large molecular weight and being slow in biodegradability was employed.

By employing a polymer according to the present invention, a sustained-release preparation (especially microspheres) having a high drug entrapment ratio and drug content with a small initial burst can be produced in a high yield. Further, a polymer of the present invention is high in safety since it is substantially free from a poisonous catalyst and organic solvent.

A sustained-release preparation of the present invention has a good dispersibility and is excellent in workability. Also, the sustained-release preparation is excellent in a storage stability and can be stored for a long time. Additionally, a sustained-release preparation of the present invention shows an almost continuous zero order release of a physiologically active substance over a long period of at least about 5 months.

What we claim is:

1. A sustained-release preparation comprising 1) a hydrolyzed polymer of lactic acid having a weight-average molecular weight of about 25,000 to about 60,000 and a dispersity of about 1.2 to about 4.0 and 2) a physiologically active substance, which preparation releases the physiologically active substance over a period of at least about 5 months.

2. The preparation according to claim 1, wherein the hydrolyzed polymer of lactic acid is obtained by hydrolyzing a polylactic acid produced by ring-opening polymerization.

3. The preparation according to claim 1, wherein the hydrolyzed polymer of lactic acid is substantially free from a catalyst.

4. The preparation according to claim 1, wherein the hydrolyzed polymer of lactic acid has a weight-average molecular weight of about 30,000 to about 50,000.

5. The preparation according to claim 1, which is for injection.

6. The preparation according to claim 1, which further comprises an excipient.

7. The preparation according to claim 6, wherein the excipient is sugar.

8. The preparation according to claim 1, wherein the physiologically active substance is a physiologically active peptide.

9. The preparation according to claim 8, wherein the physiologically active peptide is a luteinizing hormone-releasing hormone agonist or a luteinizing hormone-releasing hormone antagonist.

10. The preparation according to claim 9, wherein the luteinizing hormone-releasing hormone agonist is a peptide represented by the formula:

$$(Pyr)Glu-R_1-Trp-Ser-R_2-R_3-R_4-Arg-Pro-R_5 \qquad (I)$$

wherein $R_1$ represents His, Tyr, Trp or p-$NH_2$-Phe; $R_2$ represents Tyr or Phe; $R_3$ represents Gly or an optionally substituted D-type amino acid residue; $R_4$ represents Leu, Ile or Nle; $R_5$ represents Gly-NH-$R_6$ wherein $R_6$ is hydrogen or an alkyl group with or without hydroxy group or NH-$R_7$ wherein $R_7$ is hydrogen, an alkyl group with or without amino or hydroxy group, or ureido, or a salt thereof.

11. The preparation according to claim 10, wherein the peptide represented by the formula (I) or the salt thereof is leuprorelin or leuprorelin acetate, respectively.

12. The preparation according to claim 1, wherein the physiologically active substance is contained in an amount of about 0.01 to about 50% (w/w).

13. The preparation according to claim 1, wherein the ratio of the physiologically active substance relative to the polymer of lactic acid is about 0.01 to about 50% (w/w).

14. The preparation according to claim 1, wherein the physiologically active substance is leuprorelin acetate, the hydrolyzed polymer of lactic acid has a weight-average molecular weight of about 28,400 to about 47,800, and the preparation releases leuprorelin acetate over a period of at least about 6 months.

15. A method of producing a sustained-release preparation releasing a physiologically active substance over a period of at least about 5 months, which comprises subjecting to microencapsulation a water-in-oil emulsion with a solution containing a physiologically active substance as an internal aqueous phase and with a solution containing a hydrolyzed polymer of lactic acid having a weight-average molecular weight of about 25,000 to about 60,000 and a dispersity of about 1.2 to about 4.0 as an oil phase.

16. The preparation according to claim 1, which is for implantation.

17. The preparation according to claim 1, wherein the release of the physiologically active substance is a substantially continuous zero order release over the period of at least about 5 months.

18. The preparation according to claim 1, wherein the hydrolyzed polymer is obtained by hydrolyzing a polylactic acid produced by a ring-opening polymerization, dissolving the hydrolyzed polylactic acid in an organic solvent, injecting the obtained solution into water or a mixed solution of water and a water-soluble organic solvent, and separating a precipitated polymer of lactic acid.

\* \* \* \* \*